United States Patent [19]

Pratt, Jr. et al.

[11] 4,399,814
[45] Aug. 23, 1983

[54] METHOD AND APPARATUS FOR PRESSURE-COATED BONES

[75] Inventors: George W. Pratt, Jr., Wayland; Robert Poss, Marblehead; Timothy T. Lane, Brookline, all of Mass.

[73] Assignee: Massachusetts Institute of Technology, Cambridge, Mass.

[21] Appl. No.: 258,073

[22] Filed: Apr. 27, 1981

[51] Int. Cl.³ .............................................. A61F 5/04
[52] U.S. Cl. ................................. 128/92 C; 128/92 R; 128/92 BC; 128/92 E
[58] Field of Search .............. 128/92 C, 92 CA, 92 R, 128/92 BC, 92 E, 92 G; 3/1.9

[56] References Cited

U.S. PATENT DOCUMENTS

| | | | |
|---|---|---|---|
| 3,889,665 | 6/1975 | Ling et al. | 128/92 R |
| 4,274,163 | 6/1981 | Malcom et al. | 128/92 C |
| 4,283,799 | 8/1981 | Pratt, Jr. et al. | 3/1.9 |

*Primary Examiner*—Kyle L. Howell
*Assistant Examiner*—C. W. Shedd
*Attorney, Agent, or Firm*—Arthur A. Smith, Jr.; Thomas J. Engellenner

[57] ABSTRACT

A method of coating a portion of the walls and effecting a degree of penetration into a bone with a coating material to produce a modified bone surface, the method comprising: introducing the coating material onto the bone surface in an initial physical state; applying pressure to the coating material to force the material into the structure of the bone; and maintaining pressure on the coating material until it reaches a desired final physical state.

5 Claims, 6 Drawing Figures

METHOD AND APPARATUS FOR PRESSURE-COATED BONES

TECHNICAL FIELD

This application relates to surgical bone implants and, in particular, devices and methods for pre-coating bone cavities prior to prothetic implantations.

BACKGROUND

Approximately ten percent of the United States population suffers from some discernable sympons of arthritic disease. In the worst cases, such as osteoarthritis, the disease is characterized by deterioration of articular cartilage and loss of normal joint architecture resulting in pain and limited motion. It is estimated that about 175,000 people in this country are unable to take care of their elementary hygiene because of osteoarthritis of the hip. In some instances, rheumatoid arthritis may also produce gross destruction of the articular cartilage and render people invalid.

Rehabilitation of damaged joints therefore is of great interest. Recent advances in arthroplasty, have brought some relief from pain and improvement in gait and range of motion for those inflicted with degenerative joint diseases. In total hip arthroplasty, for example, the hip joint is replaced by a mechanical ball and socket which are implanted in the femur and pelvis, respectively.

Loosening of prothetic implants is the most prevalent problem in arthroplasty, and hip arthroplasty, in particular. For example, the Mayo Clinic has reported a 24% incidence of x-ray evidence of femoral stem loosening five to seven years post-operatively. Additionally, radiological studies have shown that as many as 87% of acetabular (hip socket) components may have a radiolucent line all the way around them at the time of ten year follow-up study. Only a small percentage of these joints are clinically loose, but the lesson to date has been that radiologic finding eventually manifest themselves as clinical symptoms. Once begun, loosening is a relentlessly progressive process. Loosening usually occurs at the bone-cement interface. The fixation at this interface is a purely mechanical one. The cement acts as a grouting agent which attempts to grip the bone by keying to irregularities on and within the cortical and cancellous surface.

A number of operative factors contribute to the weakness of the bone-cement interface. Typically, the bone surface cannot be completely cleaned of contaminants, such as blood, fat and debris. In deep cavities, such as the medullary canal of femur, there also may be inadequate filling with cement and poor mechanical keying. Bone cell death is also typical due to vascular trauma from removing the trabeculae and marrow contents followed by thermal damage from the exothermic cement polymerization reaction.

Consequently, there exists a need for improving the bond between bone and cement in arthroplasty.

SUMMARY OF THE INVENTION

We have found that the problems associated with the bone-cement interface can be reduced, if not eliminated, when a cement pre-coat is formed to coat the bone surface and penetrate into the cancellous bone. The depth of penetration may be controlled by varying the pressure under which the pre-coat cement is introduced into a bone cavity or onto a bone surface. In a simple embodiment, this method may be practiced by an inflatable bladder or an inflatable pad. Either a gas or a liquid can be used to pressurize the bladder or pad which in turn acts to drive the pre-coat cement into the bone. In other embodiments, the invention may employ more sophisticated inflatable systems, hydraulic systems, or the like, and such embodiments may also include means to dissipate heat generated by the pre-coat cement polymerization.

The fixation of a prosthetic device in some situations can be carried out in a two step process. First, a pressurized material coats the surface of the space into which at least a part of the prosthetic device is to be introduced. Secondly, the device or implant is cemented into this space. A portion of the device to be implanted in said space may itself have a cement precoating so that the second cementing step deals substantially only with a cement bond between pre-cement coated surfaces. Other situations lend themselves to a one-step process wherein cement is driven into the surface of a bone under pressure while at the same time the implant is affixed within a cavity of bone or on a bare surface or affixed to a combination of surface and cavity.

Once a bone cavity has been pre-coated with cement in accordance with our discovery, a region is formed in which the cement has been driven into the interstices of the bone tissue to form a very strong mechanical interlock. Moreover, the surface of the cavity is now prepared for implantation. The pre-coated surface permits a contaminant-free, cement/cement, interface to be formed which is about two orders of magnitude stronger than the bonding between a metallic object, such as a prosthesis stem, and the cement, because it is primarily a chemical bonding action.

Variation of the surface texture of the coating produced can also allow combinations of chemical and mechanical bonding between the coated bone surface and subsequent layers of material. Other advantages of this technique are: (a) It can produce a bone surface that is partially or completely sealed and therefore minimize contamination of that surface during subsequent procedures; (b) It can be used with cement of any viscosity (ie it can be used with coating materials of varying mechanical properties); (c) The insulator properties of the coating can reduce thermal damage to bone from heat producing steps occurring after application of the coating; (d) Multi-step coating procedures can allow use of materials with different mechanical properties and therefore affect the stress transmission from prosthesis to bone and vice-versa; and (e) Control of the temperature of the device used to create the bone pre-coat can be used to initiate and then control the rate of, and temperatures reached during chemical reactions within the coating material.

DESCRIPTION OF THE PREFERRED EMBODIMENTS

Figure 1:
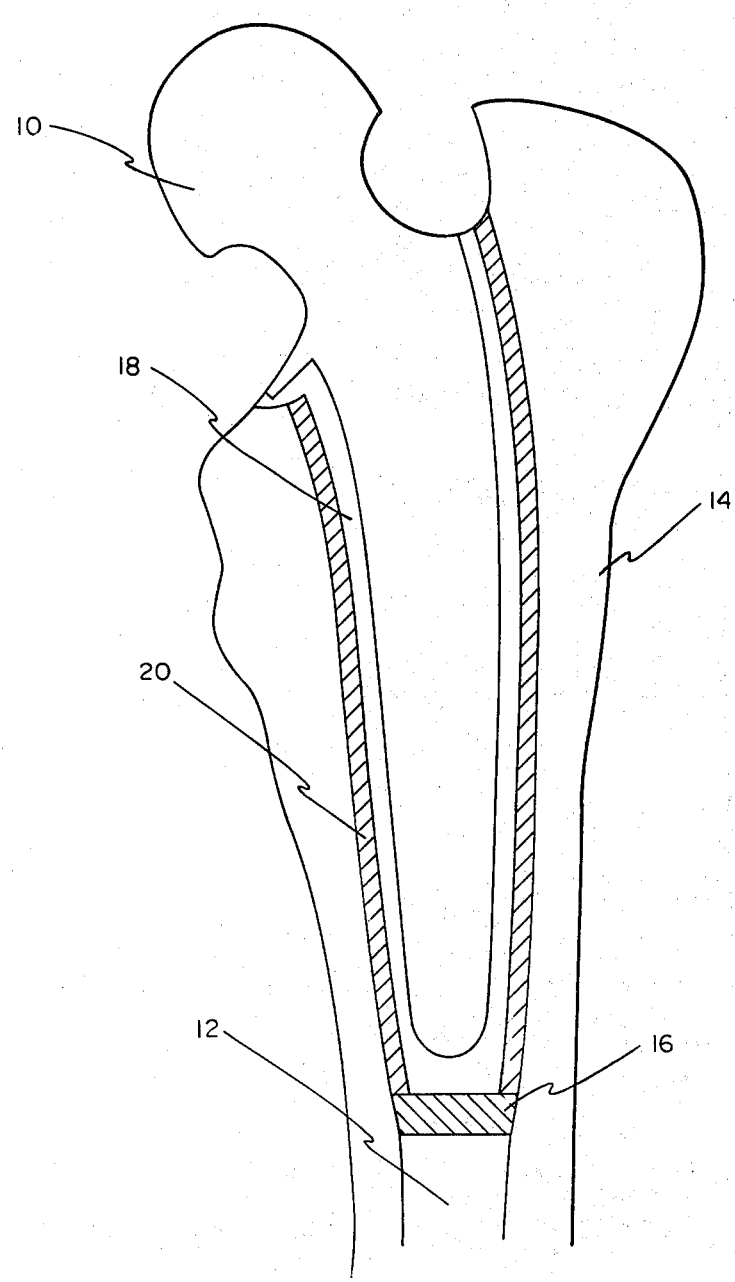
FIG. 1 is a cross-sectional, schematic, side view of a prosthetic device cemented into a pre-coated femoral bone cavity.

FIG. 1 shows in schematic form a hip prothesis 10 implanted into the medullary canal 12 of the femoral bone 14. The canal has been cleared of marrow, blood and debris and closed with a suitable plug 16 (i.e. polypropylene or the like). The prothesis 10 is secured in the canal by cement 18 and the walls of the cavity have been treated with a pre-coating 20 in accordance with out invention. Although a variety of cements may be used, one preferred cement for securing the prothesis 10, as well as for forming the pre-coating 20, is methyl methacrylate.

A number of tests have been conducted in vitro with bovine and human femoral and proximal tibial specimens using an inflatable latex bladder to force the pre-coating cement into the interstices of the cancellous bone. Both thick and thin pre-coats have been experimentally created by varying the amount of cement used to form the pre-coat. Specimens have been prepared and pre-coated at pressures ranging from 20 to 70 pounds per square inch. Some of these specimens have been x-rayed and sectioned to look at depth and quality of cement penetration. These studies revealed cancellous bone penetration of three to fifteen millimeters, depending on the technique employed, with excellent mechanical bonding.

Figure 2:
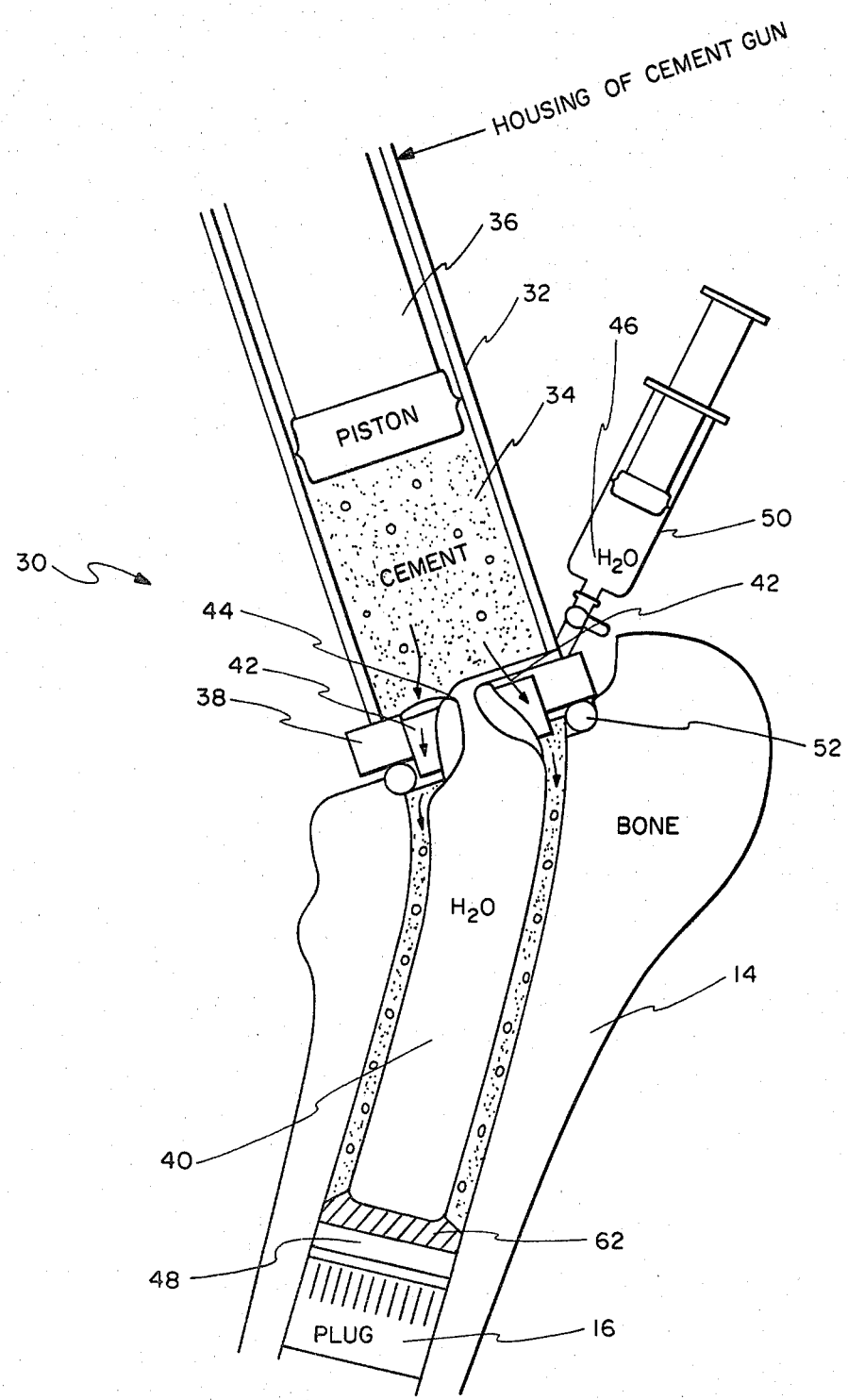
FIG. 2 is a cross-sectional, schematic, side view of a hydraulic device for pre-coating bone cavities.

In FIG. 2 a hydraulic device 30 for pre-coating a bone 14 in vivo is shown. The device 30 comprises a cement gun housing 32 positioned above the bone cavity 48. The housing 32 contains a bolus of cement 34 and a piston 36 and may be constructed as a disposable cartridge. Between the housing 32 and the bone cavity 48 is a seal 38 with holes 42 for transmitting the cement 34 from the housing 32 to the cavity 48. Seal 38 may be formed of silicone or other plastic material and is also adapted to transfer a water or saline solution 46 from a reservoir 50 to a bladder 40 of heavy latex or the like, which is situated in the cavity 40. Preferably, seal 38 included means such as collar 52 to seal and secure the device 30 to the mouth of the cavity 48. Collar 52 may also be inflatable latex and pressurized by saline or other liquid solution 46. The saline or other liquid solution can be temperature controlled to provide further control over the cement polymerization process. Thus hot saline could be used to initiate the polymerization reaction and then cooled saline used to remove heat generated internally in the cement by said process. The use of heated or cooled gas as the inflating agent would have a similar function.

In operation, for example, in the medullary cavity 48 of femur 14 shown in FIG. 2, the cavity 48 is sealed distally with plug 16 and cleaned of debris. Seal 38 is placed at the top of the cavity 48 and secured in place at the top of the cavity 48 and secured in place with bladder 40 inserted in the cavity 48. Bladder 40 may be inflated with saline 46, to determine the volume of cavity 48, and then partially deflated. Bladder 40 can have an anchoring structure 62 so that a sealed volume is defined between said structure and seal 38. This anchoring structure 62 can be any of the types described for the device in FIG. 3 (discussed below). If one of the anchoring structures that provide a permanent plugging of the cavity is used then the previously described plugging step can be eliminated. Alternative anchoring structures may also be used.

The cement gun housing 32 may then be attached to the seal 38 and the cavity 48 is filled with cement 34 by depressing piston 36. Pressurization of the cement precoat may be controlled by adjusting the volume of saline 46 in the bladder 40 and by adjusting piston 36. When the cement 34 has polymerized in the bone 14, pressure is reduced and the device 30 removed. The arthroplasty operation may then proceed.

Figure 3:
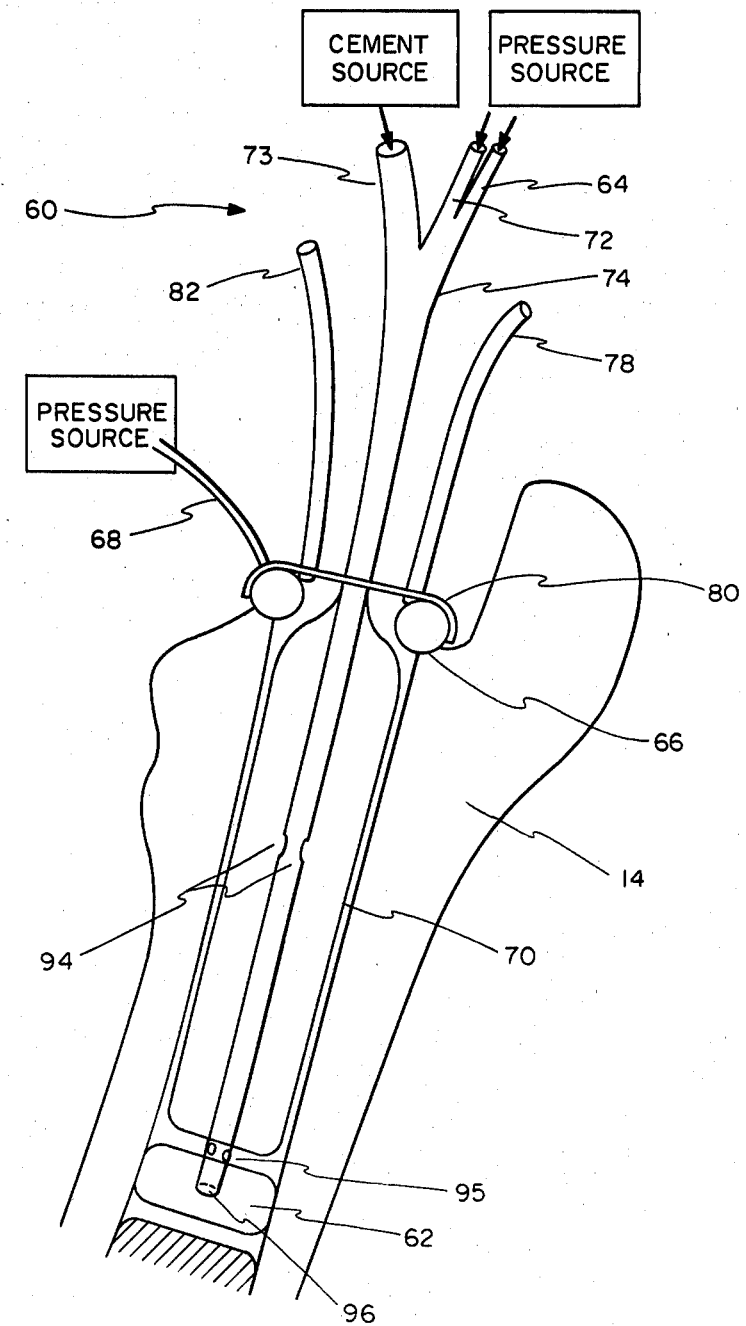
FIG. 3 is a cross-sectional, schematic side view of an inflatable bladder device for pre-coating bone cavities.

In FIG. 3 another embodiment of our device 60 for pre-coating a bone 14 in vivo is shown. The device 60 comprises a distal anchoring device 62 connected to an inflatable precoat bladder 70 and above this a proximal sealing bladder 66 and retainer plate 80 by a central structure 74. With the distal anchoring device in place and the proximal sealing bladder inflated, the volume between them 48 is now defined as the working space with which the pressurized pre-coat process is carried out.

For example, the distal anchoring device 62 can be a distal bladder which is connected by a line thru the central structure to a pressuring source. This bladder when inflated seals the cavity distally and provide an anchoring force against which the proximal sealing bladders can pull. Alternatively a conical ribbed plug of high density polyethylene or other material can be connected to the central structure via a screw thread or Luer-Lok TM type connection. This plug can seal the cavity distally and can be left in place by unscrewing the rest of the device after the pre-coating step.

Additionally, an expandable or umbrella type device can be used to open (expand) after the pre-coating device is placed in the cavity. This umbrella can be connected to the main pre-coating device by a screw thread or Luer-Lok TM. It, too, will provide a permanent distal seal and would be left in place after the pre-coating step by unscrewing it from the rest of the device.

Various other alternative anchoring devices can be devised by those skilled in the art.

The central structure 74 is comprised of a somewhat flexible multiple lumen tube. Lumens 64 and 72 carry the pressurizing agent to each bladders and to carry the coating material 73 to a discharge point 95 between the pre-coat bladders 70 and anchoring device 62.

The retainer 80 is formed with passageways for saline or other pressurizing materials—line 68, as well as passageways for suction or cement—lines 82 and 78. Alternatively cement can also be introduced into the cavity 48 by a third central lumen 73 with an opening at the bottom of the cavity as just above the anchoring structure 62.

Figure 4A:
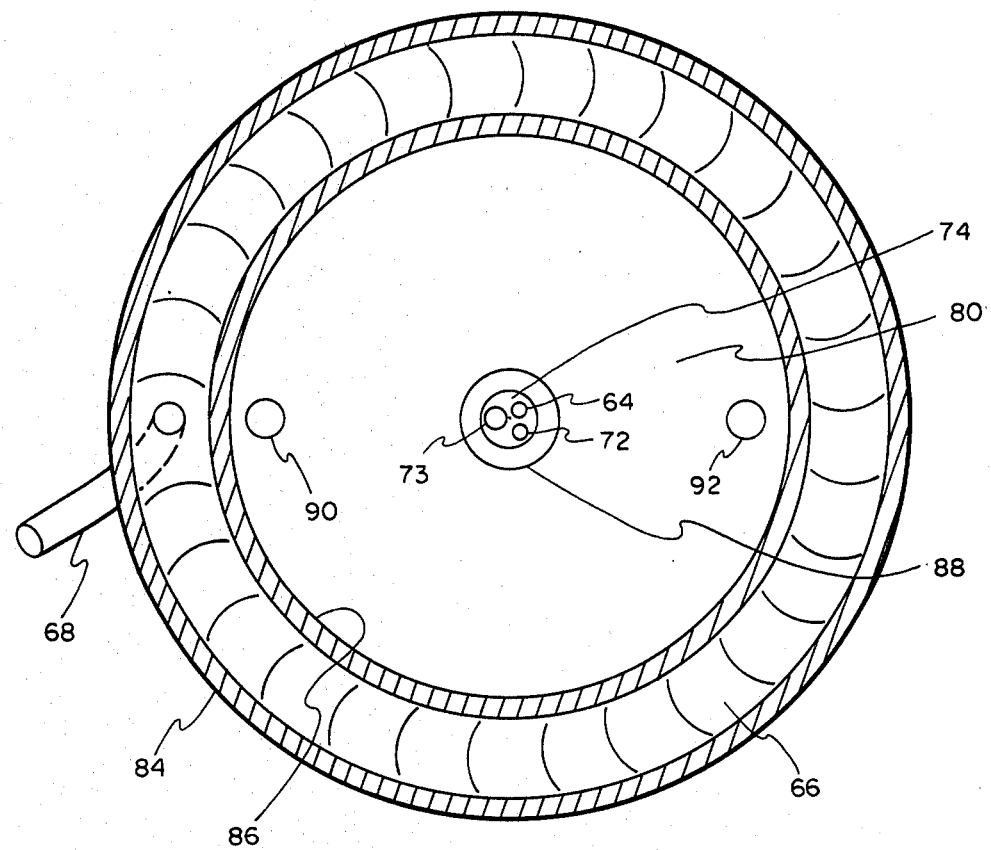
FIGS. 4a and 4b are cross-sectional, schematic, top and side views, respectively, of an upper seal plate for the devices of FIGS. 2 or 3.
Figure 4B:
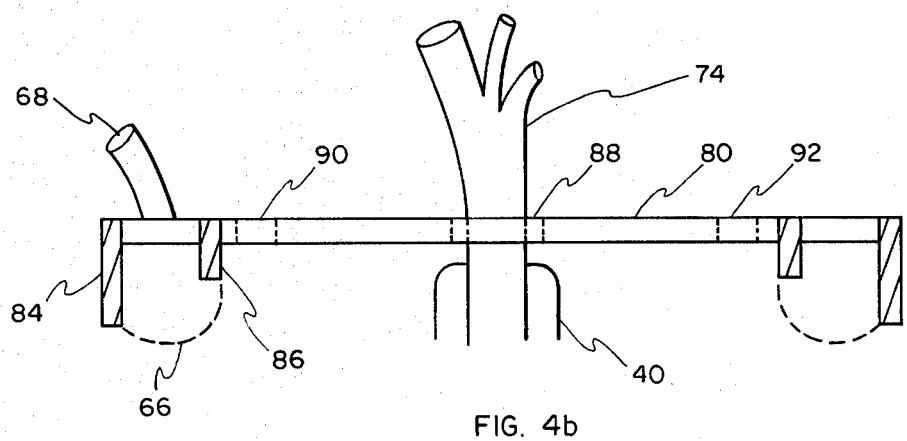

In FIGS. 4a and 4b the top retainer 80 and proximal seal bladder 66 are shown in detail. The bladder 66 sits between inner ridge 86 and outer ridge 84 formed in the retainer 80, and is connected to pressure line 68 which could carry saline solution under pressure. Passageway 88 permits the central structure 74 to enter the cavity while passageways 90 and 92 serve as inlets and/or vents for introducing cement into the cavity.

When used to pre-coat the medullary cavity of the femur, the device of FIGS. 3 and 4 can take the following dimensions. The distal anchoring device 62 may be about one-half ($\frac{1}{2}$) inch long and three-quarters ($\frac{3}{4}$) to one (1) inch in diameter to provide a suitable anchoring action against the cavity walls. The pre-coat bladder 70 may be seven (7) inches long, and three-quarters ($\frac{3}{4}$) to one (1) inch in diameter when fully inflated, holding about 50 p.s.i. The central structure 74 can be about ⅜" in diameter and contain multiple lumens sized according to the properties of the agent (pressuring agent or coating material) that they will transmit. The central lumens would terminate in holes 94, 95, 96 allowing egress of the material the lumen contains at the appropriate site.

In practice the device 60 is inserted into the cavity 48 and bladders 62 and 66 are inflated to secure the device 60 in place. Vent line 82 may be used to draw contaminants from the cavity 48. Cement is then introduced into the cavity 48 by line 78. Alternatively, lines 82 and 78 may be placed on suction and cement introduced through line 73, exiting at point 95. When the cavity 48 is filled with cement 34, lines 78 and 82 are shut and bladder 70 fully pressurized. After the pre-coating polymerizes, the bladders are deflated and the device removed. A second plug ring 16 or a bolus of cement may then be inserted in the bottom of the cavity to cover the portion of the cavity that was not pre-coated because of the presence of the anchor bladder. This step may omitted if an anchoring device that creates a permanent plug is used. The cavity is then ready for cementation of the prothesis.

Figure 5:
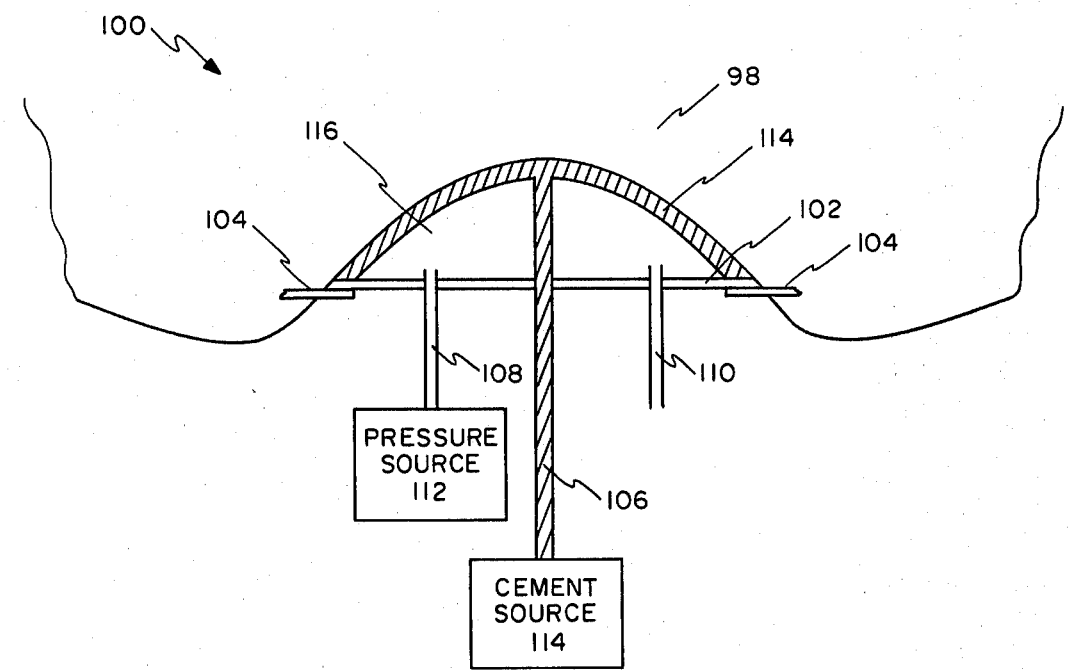
FIG. 5 is a cross-sectional, schematic, side view of an inflatable pad for pre-coating bone surfaces.

In FIG. 5, an inflatable pad structure 100 is shown for coating bone surfaces, such as an acetabulum 98, which surfaces may not be amenable for use with a distal anchor, as shown in FIGS. 2 and 3. Plate 102 defines with the acetabulum 98 a controlled volume. Plate 102 is secured in place by a plurality of pins 104. Passageway 106 serves to introduce cement 114 into the controlled volume while passageways 108 and 110 circulate a pressurizing agent 112 into and out of pad 116.

In operation the device of FIG. 2 works as follows: Plate 102 is secured in place, cement is introduced into the controlled volume, and pad 116 is inflated to force the cement into the bone structure 98.

It is apparent that various changes and modifications can be made to our devices without departing from the spirit or scope of the invention. For example, the shape of our apparatus may be modified to suit the particular bone cavity to be pre-coated. Various other anchoring means may be used in lieu of the structures shown. Although thermal damage at the time of polymerization should be minimized by the small mass of the thin pre-coat and by controlling the polymerization temperature with saline coolant in the pressurization bladder, coolants other than saline can also be used.

What we claim is:

1. A delivery device for coating a portion of, and effecting a degree of penetration into the walls of a bone with a coating material, the device comprising:
    (a) means for defining a controlled volume working space adjacent to the bone structure;
    (b) means for introducing the coating material into the working space;
    (c) pressure means for forcing the material into the structure of the walls, whereby a modified bone is produced, the pressure means comprising an inflatable bladder capable of expansion within the controlled volume to exert pressure on the coating material.

2. The device of claim 1 wherein the pressure means further comprises a hydraulic pressure means for inflating the inflatable bladder.

3. The device of claim 1 where the means for defining a controlled volume is a means for defining a controlled volume within a bone cavity, the means comprises:
    (a) an inflatable distal anchoring device secured in the bottom of the cavity; and
    (b) a proximal collar sealing plate secured at the top of the cavity, the plate having at least one hole through which the coating material is introduced.

4. The device of claim 3 wherein the proximal collar plate is sealed to the cavity walls by an inflatable cuff.

5. A cement delivery device for coating a portion of the walls and effecting a degree of penetration into the bone cavity with cement, the device comprising:
    (a) a first distal anchoring structure inflatable to secure itself to the bottom of the cavity in a fluid-tight manner;
    (b) a collar sealing plate having an inflatable cuff to seal itself in a fluid-tight manner to the top of the cavity, the plate and distal anchoring structure defining a working space controlled volume therebetween, the plate further having a plurality of passageways there through;
    (c) an inflatable pressure bladder situated within the controlled volume;
    (d) fluid delivery means for inflating said cuff, said anchoring structure and said pressure bladder, the fluid delivery means being connected to said bladders by first and second passageways in the plate; and
    (e) cement delivery means for introducing cement into the cavity and venting air and cavity debris, the cement delivery means being connected to said bladders by at least one further passageway in the plate whereby the device may be secured in place about a bone cavity by said anchor structure and said plate cuff, cement may be introduced into the cavity by the cement delivery means and may be forced into the structure of the cavity walls to produce a modified bone structure and cavity upon inflation of the pressure bladder.

* * * * *